(12) United States Patent
Ressel et al.

(10) Patent No.: US 6,274,739 B1
(45) Date of Patent: Aug. 14, 2001

(54) METHOD FOR PRODUCING CHLOROBENZOXAZOLENE

(75) Inventors: Hans-Joachim Ressel, Hattersheim; Mohammed Aslam; Jean Pierre Demoute, both of Kelkheim, all of (DE); Günter Schlegel, Tokyo (JP); Wolfgang Welter, Hofheim (DE)

(73) Assignee: Aventis CropScience GmbH, Frankfurt am Main (DE)

( * ) Notice: Subject to any disclaimer, the term of this patent is extended or adjusted under 35 U.S.C. 154(b) by 0 days.

(21) Appl. No.: 09/581,488

(22) PCT Filed: Dec. 8, 1998

(86) PCT No.: PCT/EP98/07969

§ 371 Date: Jun. 14, 2000

§ 102(e) Date: Jun. 14, 2000

(87) PCT Pub. No.: WO99/31076

PCT Pub. Date: Jun. 24, 1999

(30) Foreign Application Priority Data

Dec. 16, 1997 (DE) .............................. 197 55 904

(51) Int. Cl.[7] ................................. C07D 263/52
(52) U.S. Cl. .......................................... 548/217
(58) Field of Search ............................. 548/217

(56) References Cited

U.S. PATENT DOCUMENTS

| 4,658,034 | 4/1987 | Arndt et al. | 548/217 |
| 4,764,621 | 8/1988 | Steffan | 548/152 |

FOREIGN PATENT DOCUMENTS

| 2059725 | 6/1972 | (DE) . |
| 3234530 A1 | 3/1984 | (DE) . |
| 3406909 A1 | 9/1985 | (DE) . |

*Primary Examiner*—Deborah C. Lambkin
*Assistant Examiner*—Andrea D'Souza
(74) *Attorney, Agent, or Firm*—Frommer Lawrence & Haug LLP

(57) ABSTRACT

The invention relates to a process for preparing chlorobenzoxazoles of the formula (I),

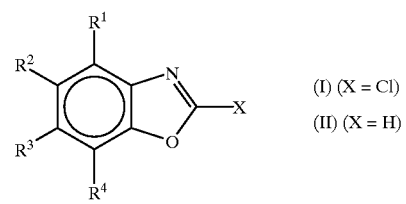

(I) (X = Cl)
(II) (X = H)

in which $R^1$, $R^2$ and $R^4$ are as defined in claim 1 and in case (a) $R^3$=H, halogen, CN, $NO_2$, $C_1$–$C_5$-alkyl, $C_1$–$C_5$-alkoxy, aryl or aryloxy, where each of the 4 lastmentioned radicals is unsubstituted or substituted, or in case (b) $R^3$=chlorine, which comprises reacting benzoxazoles of the formula (II), in which $R^1$, $R^2$ and $R^4$ are as defined in formula (I) and $R^3$ in case (a) is as defined in formula (I) and $R^3$ in case (b) is hydrogen, in the presence of an acidic catalyst with a chlorinating agent to give the monochlorination product (I) or in case (b) with an excess of the chlorinating agent to give the dichlorination product (I) in which $R^3$=chlorine.

10 Claims, No Drawings

METHOD FOR PRODUCING CHLOROBENZOXAZOLENE

This application is a 371 of PCT/EP98/07969 Dec. 8, 1998.

The invention relates to the technical field of the processes for preparing intermediates which can be employed for syntheses of active compounds, for example active compounds for crop protection agents or pharmaceuticals.

Chlorobenzoxazoles have already attained great importance as intermediates for crop protection agents and pharmaceuticals. Their properties and processes for their preparation are described, inter alia, in DE-A-3207153; EP-A-43573 and GB-A-913910.

Using processes from the abovementioned publications, chlorobenzoxazoles can be prepared, for example, from 2-mercapto-1,3-benzoxazoles by exchanging the mercapto group with chlorine using various chlorinating agents. Sulfur chlorides requiring disposal are obtained as byproducts.

A further preparation method involves appropriately substituted 1,3-benzoxazol-2-ones which are converted into chlorobenzoxazoles using an excess of phosphorus pentachloride (EP-A-572893; EP-A-141053; DE-A-3406909). In the case of the preparation of 2,6-dichlorobenzoxazole, for example, 6-chlorobenzoxazol-2-one is employed. The reprocessing of the excess of $PCl_5$ employed in this process requires a special effort.

It is already known that the unsubstituted thioanalog 1,3-benzothiazole compound can be converted into 2-chlorobenzo-1,3-thiazole by direct chlorination in the presence of chlorination catalysts (DE-A-3234530). However, this selective monochlorination reaction is not known for the analogous benzoxazole; on the contrary, DE-A-2059725 shows that in this case perchlorination occurs in the molecule, without any selectivity in the occupation of the possible substitution sites.

An alternative process for preparing chlorobenzoxazoles is required which does not have the disadvantages of the abovementioned processes. Surprisingly, it has now been found that chlorobenzoxazoles can be obtained from benzoxazoles by direct chlorination. Both monochlorinations and, alternatively, certain dichlorinations can be carried out in this process.

The invention accordingly provides a process for preparing chlorobenzoxazoles of the formula (I),

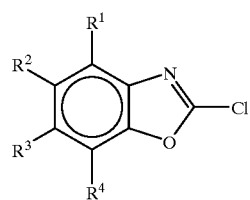

(I)

in which $R^1$, $R^2$ and $R^4$ are each, independently of one another, H, halogen, CN, $NO_2$, $C_1$–$C_5$-alkyl, $C_1$–$C_5$-alkoxy, aryl or aryloxy, where each of the 4 lastmentioned radicals is unsubstituted or substituted, and (Case a) $R^3$=H, halogen, CN, $NO_2$, $C_1$–$C_5$-alkyl, $C_1$–$C_5$-alkoxy, aryl or aryloxy, where each of the 4 lastmentioned radicals is unsubstituted or substituted, or (Case b) $R^3$=chlorine, which comprises reacting benzoxazoles of the formula (II),

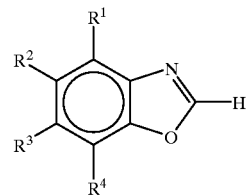

(II)

in which $R^1$, $R^2$ and $R^4$ are as defined in formula (I) and $R^3$ in case (a) is as defined in formula (I) and $R^3$ in case (b) is hydrogen, in the presence of an acidic catalyst with a chlorinating agent to give the monochlorination product (I) or in case (b) with an excess of the chlorinating agent to give the dichlorination product (I) in which $R^3$=chlorine.

According to the invention, the 2-chloroderivatives of the formula (I) can be prepared selectively in high yield and purity. Moreover, our experiments show that, if the chlorination reaction of benzoxazoles, preferably of unsubstituted benzoxazole, to the corresponding 2-chlorobenzoxazole is continued using excess chlorinating agent, 2,6-dichlorinated benzoxazoles, preferably 2,6-dichlorobenzoxazole, can be obtained selectively. Such a selectivity was unforeseeable.

Owing to the results described in DE-A-2059725 the chlorination of benzoxazole was expected to result in unselective polychlorination. Furthermore, it was not expected that the conditions described for the chlorination of benzothiazole to give 2-chlorobenzothiazole (DE-A-3234530) could be transferred to the benzoxazole molecule, since the benzoxazole skeleton and in particular benzoxazole itself is known to be a much more sensitive (reactive) molecule system and molecule, respectively. It was therefore possible to explain the technical teachings from DE-A-2059725 and DE-A-3234530 without any contradiction. Surprisingly, however, it is possible to carry out selective chlorinations under the conditions according to the invention even with benzoxazoles, and the chloroderivatives of the formula (I) are usually obtained in high yield and selectivity.

Of particular interest are processes according to the invention for preparing chlorobenzoxazoles of the abovementioned formula (I), in which $R^1$, $R^2$ and $R^4$ are each, independently of one another, H, halogen, CN, $NO_2$, $C_1$–$C_5$-alkyl, $C_1$–$C_5$-haloalkyl, $C_1$–$C_5$-alkoxy, $C_1$–$C_5$-haloalkoxy, phenyl or phenoxy, where each of the 2 lastmentioned radicals is unsubstituted or substituted by one or more radicals selected from the group consisting of halogen, CN, $NO_2$, $C_1$–$C_4$-alkyl, $C_1$–$C_4$-haloalkyl, $C_1$–$C_4$-alkoxy and $C_1$–$C_4$-haloalkoxy, preferably H, halogen, such as fluorine, chlorine, bromine or iodine, methyl, ethyl, methoxy, ethoxy, $CF_3$, $CCl_3$, $OCF_3$ or $OCHF_2$, in particular H or chlorine, and (Case a) $R^3$ in formula (I) is a radical selected from the group of the radicals possible for $R^1$, $R^2$ and $R^4$, preferably H or chlorine, or (Case b) $R^3$ in formula (I) is chlorine.

In the formulae (I) and (II), the radicals alkyl, alkoxy, haloalkyl, haloalkoxy, and also the corresponding unsaturated and/or substituted radicals, can in each case be straight-chain or branched in the carbon skeleton. Unless specifically defined, the lower carbon skeletons, for example those having 1 to 4 carbon atoms and 2 to 4 carbon atoms in the case of unsaturated groups, are preferred for these radicals.

Alkyl radicals, also in composite meanings, such as alkoxy, haloalkyl and the like, are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyls, 1-methylhexyl and 1,4-dimethylpentyl.

Halogen is, for example, fluorine, chlorine, bromine or iodine, haloalkyl, -alkenyl and -alkynyl are alkyl, alkenyl and alkynyl, respectively, which are partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl_2$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

Aryl is a monocyclic, carbocyclic aromatic ring which, in the substituted case, also includes a bi- or polycyclic aromatic system, which contains at least one aromatic ring and optionally further aromatic rings or partially unsaturated or saturated rings; aryl is, for example, phenyl, naphthyl, tetrahydronaphthyl, indenyl, indanyl, pentalenyl, fluorenyl and the like, preferably phenyl. Aryloxy is preferably an oxy radical which corresponds to the abovementioned aryl radical, in particular phenoxy.

Substituted radicals, such as substituted alkyl, aryl, phenyl or phenoxy, are, for example, substituted radicals which are derived from the unsubstituted parent compound, the substituents being, for example, one or more, preferably 1, 2 or 3, radicals selected from the group consisting of halogen, alkoxy, haloalkoxy, alkylthio, hydroxyl, amino, nitro, cyano, azido, alkoxycarbonyl, alkylcarbonyl, formyl, carbamoyl, mono- and dialkylaminocarbonyl, substituted amino, such as acylamino, mono- or dialkylamino, and alkylsulfinyl, haloalkylsulfinyl, alkylsulfonyl, haloalkyl sulfonyl and, in the case of cyclic radicals, also alkyl and haloalkyl. Preferred radicals having carbon atoms are those having 1 to 4 carbon atoms, in particular 1 or 2 carbon atoms. Preference is usually given to substituents selected from the group consisting of halogen, for example fluorine and chlorine, $C_1$–$C_4$-alkyl, preferably methyl or ethyl, $C_1$–$C_4$-haloalkyl, preferably trifluoromethyl, $C_1$–$C_4$-alkoxy, preferably methoxy or ethoxy, $C_1$–$C_4$-haloalkoxy, nitro and cyano. Particular preference here is given to the substituents methyl, methoxy and chlorine.

The starting materials, benzoxazoles of the formula (II), can be prepared in a known manner or analogously to known processes. Benzoxazoles are obtained, for example, by reacting 2-aminophenols with orthoformic esters or with formic acid or formamide (Houben-Weyl, "Methoden der organischen Chemie", Vol. E8a).

Solvents which are suitable for the chlorination reaction are organic or inorganic solvents which are inert under the reaction conditions or participate in the reaction in a suitable manner, like those which are customarily used in halogenation reactions, or mixtures thereof. In specific cases, it is also possible to employ the reaction components as solvents.

Examples of suitable organic solvents are
aromatic or aliphatic hydrocarbons, such as benzene, toluene, xylene and paraffins,
halogenated aliphatic or aromatic hydrocarbons, for example chlorinated alkanes and alkenes, chlorobenzene, o-dichlorobenzene,
nitrites, such as acetonitrile,
carboxylic acids and derivatives thereof, such as acetic acid or esters thereof.
Examples of suitable inorganic solvents are
phosphorus oxychloride or $SOCl_2$, which are additionally also suitable for use as chlorinating agents.

In an advantageous manner, it is also possible to carry out the reaction neat, i.e. in the melt of the starting material (II) or in the melt of the product (I), or in mixtures thereof.

Suitable catalysts are acidic substances or mixtures thereof, for example mineral acids or acidic salts thereof; acidic ion exchangers; zeolites (H form); other acidic minerals, such as montmorillonite, or Lewis acids, for example salts of transition metals, such as $FeHal_3$, $AlHal_3$, $Sb_2Hal_5$, $ZnHal_2$, $SnHal_2$, $SnHal_4$, $TiHal_4$, $CuHal$, $CuHal_2$, and the like; Hal is in each case a halogen selected from the group consisting of fluorine, chlorine, bromine and iodine, preferably chlorine, bromine or iodine, in particular chlorine. Preference is given to using iron (III) chloride, aluminum trichloride or montmorillonite, in particular $FeCl_3$ or $AlCl_3$.

The amount of catalyst can be varied within a wide range. The optimum amount of catalyst depends on the individual catalyst and is, for example, from 0.05 to 10 mol percent, preferably from 0.1 to 3 mol percent, of catalyst, based on the amount of compound of the formula (II) employed.

Depending on the solvent, the specific compounds of the formula (I) and (II), the catalysts and the chlorinating agent, the temperatures at which the reactions can be carried out can be varied within a wide range; suitable reaction temperatures are usually in the range of from 20 to 200° C. Depending on whether monochlorination or dichlorination is intended or whether polychlorination side reactions are possible, the reaction temperature should be chosen appropriately and, if required, be optimized in preliminary experiments. The temperature is preferably in a range of from 60 to 150° C., in particular from 80 to 140° C.

Suitable chlorinating agents are, in general, all agents which can be used for chlorinating organic compounds, or mixtures or combinations thereof. Suitable chlorinating agents are, for example, chlorine, $SO_2Cl_2$, $PCl_3$, $PCl_5$, $POCl_3$, $SCl_2$, $S_2Cl_2$, $SOCl_2$. It is also possible to use mixtures of these or with other chlorinating agents. Preference is given to introducing gaseous chlorine or using $POCl_3$, $PCl_5$ or $SOCl_2$ as chlorinating agents. Furthermore, preference is given to using a combination of $PCl_3$ and chlorine or $PCl_5$ and chlorine which generates $PCl_5$ in situ. To this end, for example, $PCl_3$ or $PCl_5$ is employed in substoichiometric amounts (in this case it is also referred to as cochlorinating agent), for example in an amount of from 0.5 to 20 mol percent, preferably 1–10 mol percent, based on the compound of the formula (II), and the remainder of chlorinating agent is introduced in the form of chlorine gas.

The amount of chlorinating agent employed is advantageously equimolar or a slight excess, preferably of from 1.0 to 1.8 mol or else 1.0 to 1.2 mol of chlorinating agent per mole of the compound of the formula (II) for monochlorination (case a), or two times the molar amount or else slightly more than two times the molar amount, preferably from 2.0 to 2.4 mol of chlorinating agent per mole of the compound of the formula (II) for dichlorination (case b). The amounts of chlorinating agent are to be reduced appropriately if the agent generates more than one molar equivalent of chlorine per mole of the agent.

The synthesis is preferably carried out by initially charging the starting material (benzoxazole derivative of the formula (II)) in the melt or in the melt of the product or in a suitable solvent and adding the catalyst. If appropriate, the cochlorinating agent, such as $PCl_3$ or $PCl_5$, is then added. At the desired temperature and with efficient stirring, chlorine is then introduced slowly, or another chlorinating agent is metered in. A considerably higher rate of conversion can be achieved by carrying out the reaction in a reactor which operates by the countercurrent principle.

The desired products are obtained selectively, in high purity and in very high yields. Very pure products can be obtained, for example, by fine distillation.

The experiments are illustrated in more detail by the examples below, without the invention being limited to these embodiments; unless stated otherwise, quantities are based on weight.

EXAMPLE 1

In a stirred flask fitted with gas inlet tube and dry-ice cooler, 20 g (0.1302 mol) of 6-chlorobenzoxazole and 50 ml of chlorobenzene were, after addition of 0.1 g of iron (III) chloride (FeCl$_3$), heated to 100° C. With efficient stirring, a total of 11.0 g (0.155 mol) of chlorine gas was introduced slowly under the surface of the liquid over a period of approximately 4 hours. The progress of the reaction was monitored by gas chromatography (GC analysis). After the starting material had been consumed, the batch was allowed to cool. According to GC analysis, 95% of the starting material was converted into 2,6-dichlorobenzoxazole. After stripping off the solvent, the crude product could be distilled under reduced pressure. This gave 23.07 g (0.122 mol) of 2,6-dichlorobenzoxazole, purity by GC: 99.5%=93.8% of theory.

EXAMPLE 2

Using the method of Example 1, 11.9 g (0.1 mol) of 1,3-benzoxazole were reacted under the same conditions to give 2-chlorobenzoxazole. This gave 14.35 g of 2-chlorobenzoxazole; GC: 99% pure=a yield of 92.5% of theory.

EXAMPLE 3

Using the method of Example 1, 11.9 g (0.1 mol) of benzoxazole were reacted, with addition of 0.5 g of montmorillonite KSF, with chlorine gas at 100° C. After addition of 1.1 times the molar amount of chlorine gas, GC showed complete conversion into 2-chlorobenzoxazole. Further introduction of chlorine gas (an additional 1.0 times the molar amount) at 120–125° C. resulted in 80.6% conversion into 2,6-dichlorobenzoxazole.

EXAMPLE 4

10 g (0.065 mol) of 6-chlorobenzoxazole (>99% pure) were dissolved in 70 ml of phosphorus oxychloride and admixed with 0.26 g of dry aluminum trichloride. The mixture was heated to 90° C., chlorine gas was then introduced, with efficient stirring, under the surface of the liquid, and the progress of the reaction was monitored by gas chromatography (GC analysis). After approximately 6 hours, the starting material had been consumed. The batch was cooled and the reaction mixture was transferred into a distillation apparatus fitted with a short Vigreux column. Excess POCl$_3$ was separated off in a forerun. A fraction of pure 2,6-dichlorobenzoxazole was subsequently distilled off under reduced pressure. This gave 11.6 g of 2,6-dichlorobenzoxazole having a purity by GC of more than 99%; this corresponds to a yield of more than 94% of theory.

EXAMPLE 5

10 g (0.065 mol) of 6-chlorobenzoxazole (>99% pure) and 100 ml of chlorobenzene, together with 13.54 g (0.065 mol) of phosphorus pentachloride and 0.05 g of iron (III) chloride (dry), were heated with stirring to 130–133° C. After approximately 6 hours, the reaction had ended. The reaction mixture was cooled and filtered through a layer of silica gel 60. Elution with methylene chloride and stripping off of the low-boilers gives a product which solidifies in the cold and which, according to GC, contains no other components; yield 12.25 g of 2,6-dichlorobenzoxazole (100% of theory).

EXAMPLE 6

With efficient stirring, 10 g (0.083 mol) of 1,3-benzoxazole (>99% pure), together with 100 ml of POCl$_3$ and 0.2 g of iron (III) chloride (dry), were heated to 100° C. At this temperature, chlorine gas was introduced under the surface of the liquid. GC control of the reaction showed that initially 2-chlorobenzoxazole was formed which, with further substitution, then reacted to give 2,6-dichlorobenzoxazole. Once all of the starting material had been consumed, the reaction was terminated. According to GC analysis, 21.5% of 2-chlorobenzoxazole and 71% of 2,6-dichlorobenzoxazol had been formed. The crude mixture was worked up by distillation. POCl$_3$ and 2-chlorobenzoxazole were collected in a first fraction and could be employed directly for a further batch. The second fraction yielded 11.0 g of 2,6-dichlorobenzoxazole (GC>99% pure) (>70% of theory). Taking into account the recycling of the 2-chlorobenzoxazole, a total yield of >92% of theory was obtained.

EXAMPLE 7

10 g (0.065 mol) of 6-chlorobenzoxazole, 0.45 g of phosphorus trichloride and 0.09 g of anhydrous aluminum trichloride were initially charged in 30 ml of phosphorus oxychloride (POCl$_3$). With heating and stirring, chlorine gas was introduced at a rate of 0.6 equivalent of chlorine per hour. After an internal temperature of 80° C. had been reached, the stream of chlorine gas was reduced to 0.6 equivalent of chlorine per 6 hours, and the temperature was increased to 100° C. The reaction was monitored by gas chromatography. After all of the starting material had been consumed, most of the POCl$_3$ was distilled off and the residue was subjected to fractional distillation under reduced pressure. This gave a pure fraction of 11.9 g of the 2,6-dichlorobenzoxazole, which solidifies on cooling (GC>99% pure) (>97% of theory).

What is claimed is:

1. A process for preparing chlorobenzoxazoles of the formula (I),

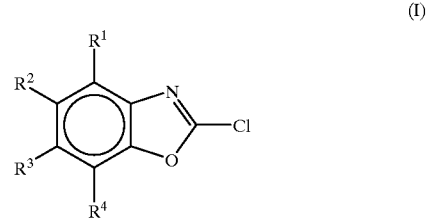

in which R$^1$, R$^2$ and R$^4$ are each, independently of one another, H, halogen, CN, NO$_2$, C$_1$–C$_5$-alkyl, C$_1$–C$_5$-alkoxy, aryl or aryloxy, where each of the 4 lastmentioned radicals is unsubstituted or substituted, and in case (a) $R^3$=H, halogen, CN, $NO_2$, $C_1$–$C_5$-alkyl, $C_1$–$C_5$-alkoxy, aryl or aryloxy, where each of the 4 lastmentioned radicals is unsubstituted or substituted, or in case (b) $R^3$=chlorine, which comprises reacting benzoxazoles of the formula (II),

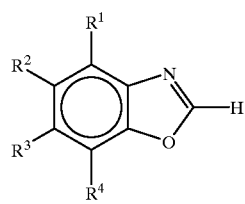

(II)

in which $R^1$, $R^2$ and $R^4$ are as defined in formula (I) and $R^3$ in case (a) is as defined in formula (I) and $R^3$ in case (b) is hydrogen, in the presence of an acidic catalyst with a chlorinating agent to give the monochlorination product (I) or in case (b) with an excess of the chlorinating agent to give the dichlorination product (I) in which $R^3$=chlorine.

2. The process as claimed in claim 1, wherein $R^1$, $R^2$ and $R^4$ in formula (I) are each, independently of one another, H, halogen, CN, $NO_2$, $C_1$–$C_5$-alkyl, $C_1$–$C_5$-haloalkyl, $C_1$–$C_5$-alkoxy, $C_1$–$C_5$-haloalkoxy, phenyl or phenoxy, where each of the 2 lastmentioned radicals is unsubstituted or substituted by one or more radicals selected from the group consisting of halogen, CN, $NO_2$, $C_1$–$C_4$-alkyl, $C_1$–$C_4$-haloalkyl, $C_1$–$C_4$-alkoxy and $C_1$–$C_4$-haloalkoxy, and (Case a) $R^3$ in formula (I) is a radical selected from the group of the radicals possible for $R^1$, $R^2$ and $R^4$ or (Case b) $R^3$ in formula (I) is chlorine.

3. The process as claimed in claim 1, wherein the compound (I) is 2,6-dichlorobenzoxazole.

4. The process as claimed in claim 1, wherein the reaction is carried out in the presence of an organic or inorganic solvent or neat.

5. The process as claimed in claim 1, wherein the chlorinating agent used is chlorine, $SO_2Cl_2$, $PCl_3$, $PCl_5$, $POCl_3$, $SCl_2$, $S_2Cl_2$, $SOCl_2$ or a mixture of the abovementioned agents.

6. The process as claimed in claim 1, wherein the chlorinating agent used is chlorine in combination with $PCl_3$ or $PCl_5$.

7. The process as claimed in claim 1, wherein the catalysts are employed in an amount of from 0.05 to 10 mol percent, based on the amount of compound of the formula (II) used.

8. The process as claimed in claim 1, wherein the catalyst employed is montmorillonite or a Lewis acid.

9. The process as claimed in claim 1, wherein the catalyst employed is $FeCl_3$ or $AlCl_3$.

10. The process as claimed in claim 1, wherein the reaction temperature is from 20 to 200° C.

* * * * *